United States Patent [19]

Rule et al.

[11] Patent Number: 4,827,018

[45] Date of Patent: May 2, 1989

[54] PROCESS FOR THE CO-PRODUCTION OF AROMATIC CARBOXYLATES AND ALKYL IODIDES

[75] Inventors: Mark Rule; Thomas H. Larkins, Jr.; Donald W. Lane; Guy R. Steinmetz, all of Kingsport, Tenn.

[73] Assignee: Eastman Kodak Company, Rochester, N.Y.

[21] Appl. No.: 112,203

[22] Filed: Oct. 22, 1987

Related U.S. Application Data

[63] Continuation-in-part of Ser. No. 922,594, Oct. 24, 1986, abandoned, which is a continuation-in-part of Ser. No. 801,903, Nov. 26, 1985, abandoned.

[51] Int. Cl.$^4$ .................... C07C 67/36; C07C 17/00
[52] U.S. Cl. .................................... 560/80; 560/97; 560/100; 560/102; 560/103; 570/181

[58] Field of Search ................ 570/181; 560/197, 100, 560/80, 102, 103

[56] References Cited

U.S. PATENT DOCUMENTS

| | | | |
|---|---|---|---|
| 2,565,462 | 8/1951 | Prichard et al. | 560/97 |
| 2,565,464 | 8/1951 | Tabet | 560/97 |
| 2,640,071 | 5/1953 | Leibu | 560/97 |

Primary Examiner—Werren B. Lone
Assistant Examiner—Vera C. Clarke
Attorney, Agent, or Firm—Charles R. Martin; J. Frederick Thomsen

[57] ABSTRACT

Disclosed is a process for the co-production of aromatic carboxylates and alkyl iodides by the carbonylation of aromatic iodides in the presence of an alkanol and a nickel catalyst.

11 Claims, No Drawings

PROCESS FOR THE CO-PRODUCTION OF AROMATIC CARBOXYLATES AND ALKYL IODIDES

This is a continuation of application Ser. No. 922,594 filed on Oct. 24, 1986, which in turn is a continuation-in-part of application Ser. No. 801,903 filed Nov. 26, 1985, both now abandoned.

DESCRIPTION

This invention relates to a novel carbonylation process for the preparation of both aromatic carboxylic acids or esters and an iodine containing compound from which the iodine values can be economically recovered. The carbonylation is conducted in the presence of an alkanol and a catalytic amount of nickel.

The carbonylation of aromatic halides in the presence of nickel to obtain aromatic carboxylic acids and esters as well known in the art. Nakayama and Mizoroki (Bull. Chem. Soc. Japan 42, 1124 (1969)) discloses the carbonylation of aromatic halides in the presence of an alcohol and a potassium acetate to produce the corresponding carboxylic acid ester.

While it is known that aromatic iodides can be carbonylated the use of these materials has been discouraged by the cost associated with the difficulty of recovering the iodine values. For example, the use of basic materials in the carbonylation of aromatic halides, such as potassium acetate by Nakayama and Mizoroki, results in the formation of halide salts from which the halide values can be reclaimed only through uneconomical procedures involving severe chemical treatments.

We have discovered a process which not only results in the carbonylation of aromatic iodides to aromatic carboxylic acids or esters in excellent yields and at excellent rates of conversion but also results in production of alkyl iodides from which the iodine values can be economically recovered. In this invention the carbonylation is conducted in the presence of an alkanol and a catalytic amount of a nickel catalyst under aromatic carboxylic ester and alkyl iodide-forming conditions of temperature and pressure. The advantage afforded by our invention over the prior art is that the iodine values in the alkyl iodide may be readily recovered by simply flashing the relatively volatile alkyl iodide from the mixture resulting from the carbonylation reaction. This can be accomplished either in the carbonylation reactor or, more preferably, in a pressure reduction vessel to which the mixture resulting from the carbonylation reaction is fed.

The ratio of aromatic acids to esters produced in the present invention is dependent on the ratio of alkanol to water present in the carbonylation reactor and on the choice of organic co-solvent. In general, minimizing the ratio of alkanol to water maximizes the production of acid. Conversely maximizing the ratio of alkanol to water maximizes the production of ester.

The aromatic iodides which may be used in our process may be monoiodo or polyiodo, e.g. di-, tri- and tetra-iodo aromatic compounds. The aromatic nucleus or moiety can contain from 6 to 18 carbon atoms, preferably 6 to 10 carbon atoms and may be carbocyclic aromatic such as benzene, biphenyl, terphenyl, naphthalene, anthracene, etc., or heterocyclic aromatic such as pyridine, thiophene, pyrrole, indole, etc. In addition to one or more iodine atoms, the aromatic moiety may be substituted by various substituents inert under the conditions employed in our process. Examples of such substituents include alkyl of up to about 12 carbon atoms such as methyl, ethyl, isobutyl, hexyl, 2-ethylhexyl, nonyl, decyl, dodecyl, etc.; cycloalkyl of about 5 to 12 carbon atoms such as cyclopentyl, cyclohexyl, 4-butylcyclohexyl, etc.; hydroxy; alkoxy of up to about 12 carbon atoms such as methoxy, ethoxy, propoxy, butoxy, octyloxy, etc.; halogen such as chloro and bromo; alkoxycarbonyl of from 2 to about 8 carbon atoms such as methoxycarbonyl, ethoxycarbonyl, butoxycarbonyl, hexyloxycarbonyl, etc.; carboxyl; cyano; alkenyl of about 2 to 12 carbon atoms such as vinyl, allyl, etc.; formyl; alkanoyl of about 2 to 8 carbon atoms such as acetyl, propionyl, butyryl, hexanoyl, etc.; alkanoylamido of about 2 to 8 carbon atoms such as acetamido, butylamido, etc.; aroylamino such as benzamido; and alkylsulfonamide such as methanesulfonamido, hexanesulfonamido, etc.

Specific examples of the aromatic iodide reactants include iodobenzene, 1,3- and 1,4-diodobenzene, 1,3,5-triiodobenzene, 4-iodotoluene, 4-iodophenol, 4-iodoanisole, 4-iodoacetophenone, 4,4'-diiodobiphenyl, 4-chloroiodobenzene, 3-bromoiodobenzene, and 2,6- and 2,7-diiodonaphthalene. Our process is particularly useful for the preparation of benzenedicarboxylic and naphthalenedicarboxylic acids and their esters and thus the preferred reactants are diiodobenzenes, especially 1,3- and 1,4-diiodobenzene, and diiodonaphthalenes, especially 2,6- and 2,7-diiodonaphthalene.

The aromatic iodide reactants are known compounds and/or can be prepared according to published procedures. For example, T. Hudlicky et al *The Chemistry of Halides, Pseudohalides and Azides*, Supplement D, Part 2, 1142–1158, the disclosure of which is incorporated herein by reference in its entirety, discloses a number of such processes. Another process described in J. Chem. Soc. 150 (1952) comprises treating an aromatic compound, such as benzene, with iodine in the presence of silver sulfate dissolved in concentrated sulfuric acid.

The alkanol used in the process of this invention normally is methanol since it is the least expensive, results in the formation of methyl carboxylate esters, which may be used in transesterification reactions, and produces methyl iodide which is the most volatile of the alkyl iodides. However, other alkanols, for example, alkanols containing up to about 12 carbon atoms, preferably up to about 4 carbon atoms, may be employed if desired. Examples of such alkanols include ethanol, propanol, butanol, pentanol, hexanol, heptanol, octanol, decanol, ethylene glycol, diethylene glycol, benzyl alcohol, and the like. If aromatic esters are desired, about two moles of alkanol are required for each mole equivalent of iodoaromatic reacting. For each mole equivalent of aromatic acid produced, one mole of alkanol is required.

The process provided by our invention can also be carried out in the presence of an organic co-solvent such as aliphatic, alicyclic and aromatic hydrocarbons, halogenated hydrocarbons and ethers. Examples of such inert solvents include benzene, toluene, the xylenes, hexane, heptane, chlorobenzene, ethylene dichloride, methylchloroform, diethyl ether, methyl t-butyl ether, diglyme, acetic acid, benzoic acid, methyl benzoate, etc. However, the use of a co-solvent is not critical to the practice of this invention.

The nickel catalyst can be provided to the reaction medium as either nickel metal or as any of a number of nickel salts or complexes, such as nickel iodide. The amount of nickel is not significant as long as enough is present to catalyze the reaction. Preferably, the catalyst is present in a concentration of 10 to 0.001 mole percent, preferably 2.5 to 0.1 mole percent, based on the moles of aromatic iodide reactant. Therefore, the total reaction medium has a catalyst concentration of about 10,000 ppm to 1 ppm with preferred catalyst concentrations of 2,500 to 100 ppm.

The carbonylation reaction is conducted in the presence of carbon monoxide, which is employed in amounts such that the total reaction pressure is suitable for the formation of both the aromatic carboxylic ester and the alkyl iodide. The carbon monoxide employed may be essentially pure or it may contain other gases such as carbon dioxide, hydrogen, methane and other compounds produced by synthesis gas plants. Normally, the carbon monoxide will be at least 90, preferably at least 95, percent pure.

The process of the present invention can be conducted at temperatures and pressures suitable for formation of both the aromatic carboxylic acid and alkyl iodide. The temperatures and pressures are interdependent and can vary considerably. Normally, the pressure will be at least 100 psig. While the process can be carried out at pressures as high as 10,000 psig, the cost of utilities and equipment required for such high pressure operation cannot normally be commercially justified. Thus, the pressure normally will be in the range of about 125 to 4000 psig, preferably about 300 to 1000 psig. A particularly preferred pressure is 750 to 1000 psig. While temperatures as low as 125° C. and higher than 225° C. may be used, our process normally is carried out between about 125° to 225° C. The preferred temperature range is 150° to 200° C.

The relative amounts of carbon monoxide, alkanol and aromatic iodide used in our process can be varied substantially and are, in general, not critical as long as there is at least a stoichiometric amount present.

When a polyiodo aromatic compound is used as the reactant in our carbonylation process, the products obtained include both aromatic polycarboxylic esters and partially carbonylated products such as iodo aromatic carboxylic esters. The latter compounds are useful as intermediates in the preparation of derivatives of aromatic carboxylic esters, for example, by displacement reactions whereby the iodo substituent is replaced with other radicals. The difunctional esters, such as dimethyl 2,6-naphthalene dicarboxylate, can be reacted with diols to produce high molecular weight polyesters suitable for molding plastics. Useful articles can be molded from these plastics, such as by injection molding. The relative amounts of partially or totally carbonylated products is highly dependent on the period of time that the reactant resides under carbonylation conditions. For example, the carbonylation of diiodobenzene at 175° C. and 750 psig in accordance with our invention over varying periods of time results in varying amounts of reactant, iodo ester and diester.

The alkyl iodides prepared according to the process of our invention may be used in other chemical processes such as in the preparation of carboxylic acids and carboxylic anhydrides according to known carbonylation procedures. Alternatively, the alkyl iodide can be oxidatively decomposed at elevated temperature to produce a gaseous mixture of iodine, carbon dioxide and water from which the iodine can be recovered. Alternatively, the alkyl iodides may be thermally decomposed to iodine and an alkane.

Our process is carried out at a pKa of less than 5. Therefore, there are no significant amounts of basic materials which preferentially combine with hydrogen iodide and interfere with the formation of an alkyl iodide. Examples of such bases which are not present in significant amounts in our process include amines, particularly tertiary amines, and hydroxides, alkoxides and weak acid salts, e.g. carboxylates, of the alkali and alkaline earth metals.

Our process is particularly useful for the preparation of dialkyl esters of aromatic dicarboxylic acids such as 1,3- and 1,4-benzenedicarboxylic and 2,6- and 2,7-naphthalenedicarboxylic acid esters. Such diesters may be used in the preparation of polyesters such as poly(ethylene terephthalate) and poly(ethylene 2,6-naphthalenedicarboxylate).

The process of this invention can be carried out as a batch, semi-continuous or continuous operation. In the manufacture of dialkyl esters of aromatic dicarboxylic acids in the quantities required for use in the preparation of polyesters such as those mentioned above, the process described hereinabove usually will be carried out in a continuous manner. A typical continuous method of practicing our process comprises feeding a solution of an aryl iodide, alkanol and catalyst to the base of a back mixed pressure vessel equipped with means for maintaining the temperature and pressure therein at the desired carbonylation conditions of temperature and pressure. Reaction mixture which overflows the reactor is passed, after reducing the pressure, to a flash pot from which the alkyl iodide, some of the alkanol and some nickel carbonyl is flashed off. The vapor stream is submitted to a scrubbing operation using iodine in an alkanol to recover the nickel values therefrom as a solution of nickel iodide in the alkanol. The scrubbed vapor stream can be submitted to further processing to obtain essentially pure alkyl iodide or the stream can be treated as described hereinabove to recover the iodine therefrom. The liquid phase from the flash pot can be cooled to precipitate the alkyl aromatic carboxylate product or products which may be isolated by filtration. The isolated crude product can be further purified, for example, by selective recrystallization, to separate the desired product from other products such as partially-carbonylated compounds and from any starting material present. The liquid streams from the above-described operations can be returned to the reactor.

Our invention is further illustrated by the following examples. In the procedures utilized in the examples the materials employed are loaded into a 330 ml autoclave constructed of Hastelloy B2 alloy which is designed to operate in a rocking mode. The autoclave is pressurized with 500 psig carbon monoxide gas pressure at room temperature and then the gas is vented and the autoclave is sealed. In Examples 1-9 the autoclave is pressurized to 100 psig with carbon monoxide gas at ambient temperature and heated and rocked until reaction temperature was reached, at which time additional carbon monoxide gas is added to increase the autoclave internal pressure to the predetermined value. Reactor pressure is maintained by adding carbon monoxide at the same rate at which it is consumed by the reactants. The carbon monoxide used is essentially pure. When the predetermined reaction time is completed the autoclave is cooled by a stream of cold air to approximately 25° C. After the gas is vented from the autoclave the crude product is isolated by filtration and analyzed by gas chromatographic methods. The % conversion is the mole percent of iodo-group converted to carboxylic acid or ester. The ester/acid ratio is the mole ratio of total ester and acid groups formed. The grams of alkyl iodide found were determined by gas chromatographic analysis of the reaction solution. The results of these runs are shown below.

| Example No. | 1 | 2 | 3 | 4 |
|---|---|---|---|---|
| Iodoaromatic | p-diiodobenzene | p-diiodobenzene | p-diiodobenzene | p-diiodobenzene |
| wt (g) | 20 | 40 | 20 | 20 |
| Alkanol | methanol | methanol | methanol | methanol |
| wt (g) | 20 | 16 | 24 | 24 |
| Co-Solvent | acetic acid | toluene | o-xylene | tetrahydrofuran |
| wt (g) | 79 | 69 | 59 | 58 |
| Catalyst | Ni(OAc)$_2$.4H$_2$O | Ni(OAc)$_2$.4H$_2$O | Ni(OAc)$_2$.4H$_2$O | Ni(OAc)$_2$.4H$_2$O |
| wt Ni(g) | 0.40 | 0.40 | 0.40 | 0.40 |
| Time (Hr) | 3 | 2 | 3 | 3 |
| Pressure (psig) | 1000 | 1000 | 750 | 750 |
| Temp (°C.) | 190 | 190 | 175 | 175 |
| % Conversion | 99 | 100 | 100 | 100 |
| Ester/Acid | 0.08 | 3 | 10 | 6 |
| g. Alkyl Iodide | 15 | 29 | 15 | 15 |

| Example No. | 5 | 6 | 7 | 8 |
|---|---|---|---|---|
| Iodoaromatic | p-diiodobenzene | p-diiodobenzene | p-diiodobenzene | 2,6-diiodonaphthalene |
| wt (g) | 20 | 20 | 20 | 40 |
| Alkanol | methanol | methanol | ethanol | methanol |
| wt (g) | 10 | 75 | 75 | 16 |
| Co-Solvent | methyl t-butyl ether | — | — | toluene |
| wt (g) | 40 | | | 70 |
| Catalyst | NiI$_2$ | Ni(OAc)$_2$.4H$_2$O | Ni(OAc)$_2$.4H$_2$O | NiI$_2$ |
| wt Ni(g) | 0.19 | 0.40 | 0.40 | 0.38 |
| Time (Hr) | 3 | 3 | 3 | 4 |
| Pressure (psig) | 750 | 750 | 750 | 750 |
| Temp (°C.) | 175 | 175 | 175 | 170 |
| % Conversion | 50 | 67 | 100 | 100 |
| Ester/Acid | 5 | 5 | 5 | 7 |
| g. Alkyl Iodide | 7 | 10 | 16 | 25 |

The invention has been described in detail with particular reference to preferred embodiments thereof, but it will be understood that variations and modifications can be effected within the spirit and scope of the invention.

We claim:

1. A process comprising producing a mixture of an aromatic carboxylic ester and an alkyl iodide by carbonylating an aromatic iodide in the presence of carbon monoxide, an alkanol and a catalytic amount of a nickel catalyst in the range of 10 to 0.001 mole percent under aromatic carboxylic ester and alkyl iodide forming conditions of temperature and pressure, and recovering said alkyl iodide so produced.

2. The process of claim 1 wherein the aromatic iodide is selected from the group consisting of diiodonaphthalene and diiodobenzenes.

3. The process of claim 2 wherein the diiodonaphthalene is 2,6-diiodonaphthalene and the diiodobenzene is 1,4-diiodobenzene.

4. The process of claim 1 wherein the alkanol is methanol.

5. The process of claim 1 wherein the temperature is in the range of about 125° to 225° C.

6. The process of claim 5 wherein the temperature is in the range of about 150°–200° C.

7. The process of claim 1 wherein the pressure is in the range of 125 to 4,000 psig.

8. The process of claim 7 wherein the pressure is in the range of 300 to 1,000 psig.

9. The process of claim 1 wherein the process is carried out in the presence of an organic co-solvent.

10. A process comprising producing mixture of an aromatic dicarboxylic ester selected from the group consisting of dimethyl benzenedicarboxylate and dimethyl naphthalenedicarboxylate and methyl iodide by carbonylating a diiodoaromatic compound selected from the group consisting of diiodobenzene and diiodonaphthalene in the presence of carbon monoxide, methanol, an organic co-solvent and a catalytic amount of a nickel catalyst in the range of 10 to 0.001 mole percent at a temperature of about 150° to 200° C. and a pressure of about 300 to 1,000 psig, and recovering the methyl iodide so produced.

11. A process comprising producing a mixture of dimethyl 2,6-naphthalenedicarboxylate and methyl iodide by carbonylating 2,6-diiodonaphthalene in the presence of carbon monoxide, methanol, an organic co-solvent and a catalytic amount of nickel in the range of 10 to 0.001 mole percent at a temperature of about 175° C. and a pressure of about 750 psig, and recovering the methyl iodide so produced.

* * * * *